United States Patent
Burrell et al.

(10) Patent No.: US 7,499,160 B2
(45) Date of Patent: Mar. 3, 2009

(54) METHODS FOR AMPLIFYING THE RAMAN SIGNAL OF SURFACE ENHANCED RAMAN SCATTERING NANOPARTICLES

(75) Inventors: Michael Burrell, Clifton Park, NY (US); Frank John Mondello, Niskayuna, NY (US); Tracy Lynn Paxon, Waterford, NY (US)

(73) Assignee: GE Homeland Protection, Inc., Newark, CA (US)

( * ) Notice: Subject to any disclaimer, the term of this patent is extended or adjusted under 35 U.S.C. 154(b) by 281 days.

(21) Appl. No.: 11/602,755

(22) Filed: Nov. 21, 2006

(65) Prior Publication Data
US 2008/0118986 A1    May 22, 2008

(51) Int. Cl.
*G01J 3/44* (2006.01)
*G01N 21/65* (2006.01)

(52) U.S. Cl. ...................................................... 356/301
(58) Field of Classification Search .................. 356/301
See application file for complete search history.

(56) References Cited

U.S. PATENT DOCUMENTS 6,149,868 A * 11/2000 Natan et al. .................. 356/301
6,861,263 B2 * 3/2005 Natan ........................... 356/301

OTHER PUBLICATIONS

Thomas et al. "Conjugation to gold nanoparticles enhances polyethlenimine's transfer of plasmid DNA into mammalian cells", Department of Chemistry and Division of Biological Engineering, Massachusetts Institute of Technology, Cambridge, MA, Aug. 5, 2003, www.pnas.org/cgi/doi/10.1073/pnas.1233634100, pp. 9138-9143.

Liz-Marzan et al. "Synthesis of Nanosized Gold—Silica Core—Shell Particles", 1996 American Chemical Society, pp. 4329-4335.

* cited by examiner

*Primary Examiner*—F. L Evans
(74) *Attorney, Agent, or Firm*—Richard A. DeCristofaro (57) ABSTRACT

Methods for amplifying the Raman signal of primary SERS nanoparticles are provided. One method generally includes binding secondary SERS particles to the primary SERS nanoparticles after binding of the primary SERS nanoparticles. In another method, secondary SERS nanoparticles are brought in close proximity to the primary SERS nanoparticles, wherein the secondary nanoparticles are free of a reporter molecule or have a reporter molecule different from that of the primary SERS nanoparticles.

23 Claims, 6 Drawing Sheets

METHODS FOR AMPLIFYING THE RAMAN SIGNAL OF SURFACE ENHANCED RAMAN SCATTERING NANOPARTICLES

BACKGROUND OF THE INVENTION

The disclosure generally relates to methods for amplifying the Raman signal of surface enhanced Raman scattering (SERS) nanoparticles.

Surface enhanced Raman scattering allows for the detection of molecules attached to the surface of a single metallic nanoparticle, typically a gold or silver nanoparticle. Existing SERS nanoparticles, also referred to as nanotags, generally include the metallic nanoparticle having a reporter molecule in close proximity thereto (typically less than 50 angstroms), which produces a strong Raman signal due to a surface enhanced effect. Bringing reporter molecules in close proximity to the metal surfaces is typically achieved by adsorption of the Raman-active molecule onto suitably roughened metal nanoparticles, e.g., gold, silver, copper, or other free electron metals. The characteristic signal of the reporter molecule is used to determine the presence and amount of the SERS nanoparticles. Consequently, SERS nanoparticles have utility as spectroscopic and optical tags and are often used in assays.

SERS nanoparticles are somewhat versatile and can be functionalized with biological molecules (e.g., antibodies, DNA, and the like) so that they specifically bind to one kind of target (e.g., specific types of bacteria, viruses, spores, proteins, DNA, and the like). For example, SERS nanoparticles can be used in immunoassays when conjugated to an antibody against a target of interest. If the target of interest is immobilized on a solid support, then the interaction between a single target and a single nanoparticle-bound antibody could be detected by searching the unique Raman spectrum for the Raman-active reporter molecule. Furthermore, because a single Raman spectrum (from 100 to 3500 $cm^{-1}$) can detect many different Raman-active molecules, SERS nanoparticles can often be used in multiplexed assay formats.

SERS is believed to occur primarily as a result of surface plasmon resonances in the metal nanoparticle that enhance the local intensity of the light, and formation and subsequent transitions of charge-transfer complexes between the metal surface and the Raman-active reporter molecule.

Protocols for producing SERS nanoparticles from colloidal solutions of metallic nanoparticles present formidable practical problems. For example, metal nanoparticles are exceedingly sensitive to aggregation in aqueous solution; once aggregated, re-dispersion is generally impossible. In addition, the chemical compositions of some Raman-active reporter molecules are incompatible with the chemistries used to attach other molecules (such as proteins) to the metal nanoparticles. This restricts the choices of Raman-active reporter molecules, attachment chemistries, and other molecules to be attached to the metal nanoparticle.

By design, the Raman spectroscopic signal from a SERS nanotags is dominated by the surface-enhanced Raman spectrum of the attached reporter molecule. Other attached moieties, such as the recognition element (e.g., antibody), or encapsulating shells (e.g., glass), do not contribute to the observed Raman spectrum because they are either Raman inactive, their Raman signal is not surface-enhanced due to the particular bonding geometry, their distance from the metal surface is too great, or other reasons.

Figure 1:
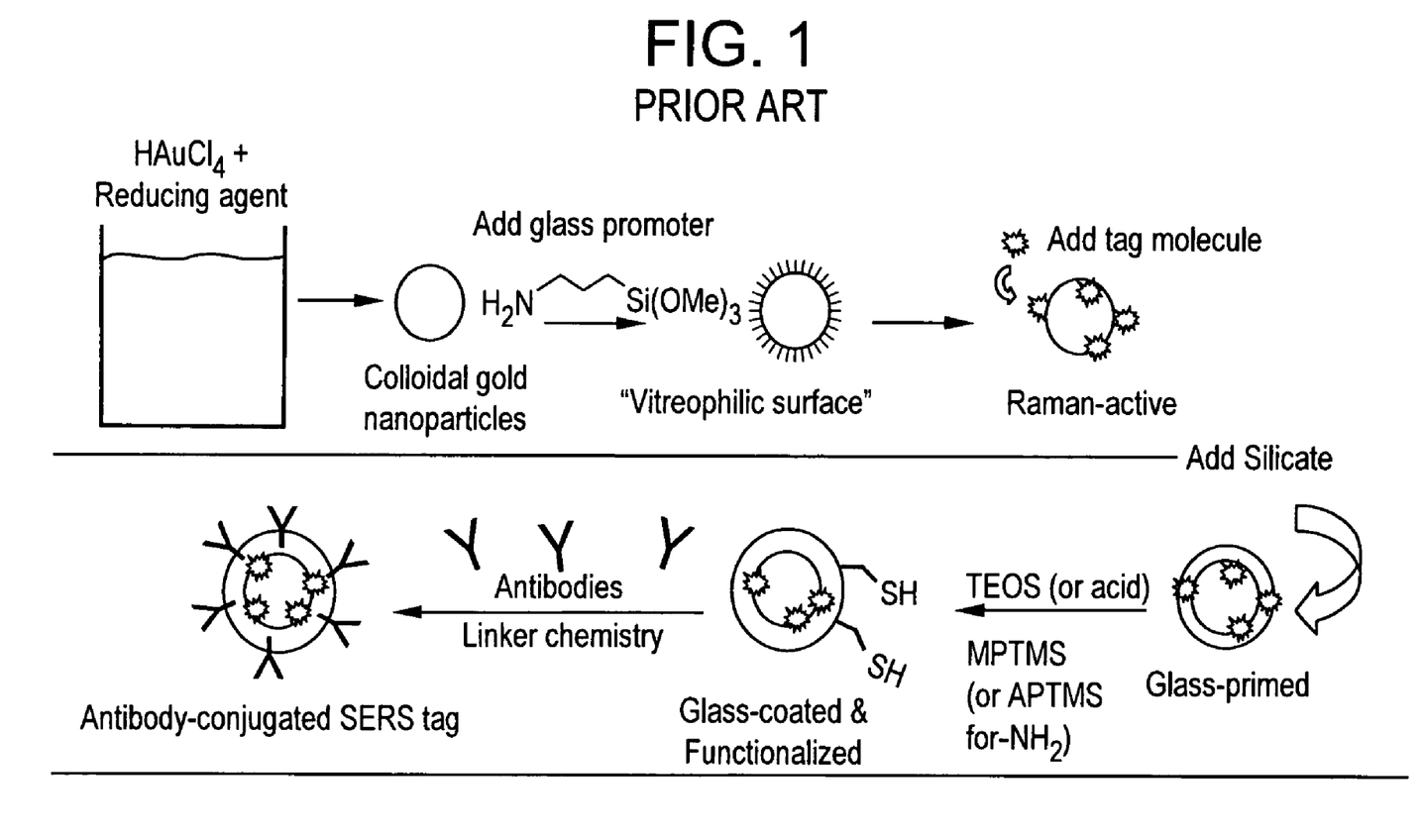
FIG. 1 is a prior art schematic illustrating a synthetic pathway for producing SERS nanoparticles.

Current processes for making the SERS nanoparticles are numerous. One method as described in U.S. Pat. No. 6,514,767 to Natan generally follows a synthetic pathway as outlined in the schematic provided in prior art FIG. 1. The synthetic pathway generally starts with a colloidal solution, e.g., $HAuCl_4$ (i.e., gold chloride) colloidal solution, and a reducing agent that results in the precipitation of gold nanoparticles having average diameters of about 60 nm. The reducing agent is composed of a single reductant, typically a citrate salt, e.g., sodium citrate, to reduce the gold and form a stable colloid. The resulting colloid is generally red in color and exhibits an absorption peak ($\lambda_{max}$) at about 530 nm. An amino-based silane is then added to form vitreophilic surfaces capable of accepting the desired tag or reporter molecules. Next, a silicate is added, which polymerizes onto the "tagged" gold nanoparticle surface. The thickness of the silicate layer is typically on the order of a few nanometers. A thicker shell can be formed if desired using tetraethylorthosilicate (TEOS). During or after this step, the glass-coated nanoparticle can also be functionalized such as with 3-mercaptopropyltrimethoxysilane (MPTMS) or 3-aminopropyltrimethoxysilane (APTMS) to form SERS nanoparticles with corresponding end groups having sulfhydryl or amino functionalization. Optionally, a second silane-coupling agent can be used depending on the polarity of the solvent in which the particles are to be dispersed. In this manner, the nanoparticles can be dispersed in a low polarity solvent if desired for the particular application. Target molecules with the appropriate linker chemistry are reacted with the end groups to provide the tagged SERS nanoparticles. For example, antibody conjugated SERS nanoparticles can be formed.

Other methods for producing SERS-active nanotags provide different particle architectures. For example, Nie and Doering as described in PCT Application No. WO 2005/062741 used organic dyes adsorbed to a metallic core, and also encapsulated the resulting particle with a glass shell. In U.S. Patent Publication No. US20050089901 A1 to Porter, a tag is built from a metal nanoparticle core, and in this case, the Raman-active molecule is specifically chosen to have a reactive end that binds to the metal nanoparticle surface and another part that acts as a linker to the biological attachment part, so that the overall SERS nanotags does not have a glass shell. In US Published Patent Application No. 2005/0158877 A1 to Wang et al., analyte analogues are first attached to a metallic particle surface. Then the metallic colloidal solution is mixed with an antibody solution. Each antibody molecule will bind with two analyte analogue molecules, thus causing the metallic particles to aggregate and form a cluster structure for SERS signal amplification. In the presence of analyte, the antibody molecule reacts with the analyte molecule and the formation of the cluster structure is inhibited, which results in a decrease of the Raman signal. Thus the presence and amount of the analyte can be inferred from the intensity variation of the Raman signals. In each instance, each SERS particle has both the Raman dye and the antibody.

During the preparation of SERS nanotags, starting with a colloidal solution of metallic nanoparticles, it is often observed that the Raman signal of the adsorbed reporter molecule is substantially enhanced when the metallic nanoparticles begin to aggregate due to addition of an excess amount of the reporter molecule, or an excess of another adsorbate along with the reporter molecule. However, gross aggregation prevents further processing of the SERS nanotags, since they begin to form precipitates that are not re-dispersible, and are often not amenable to further modification such as antibody attachment. Thus, protocols for preparation of SERS nanotags are designed to eliminate or minimize aggregation.

Regardless of the method used for producing the SERS active nanoparticles, there remains a need in the art for amplification of the Raman signal to improve the detection limits especially with regard to the SERS nanoparticles.

SUMMARY OF THE INVENTION

Processes for amplifying the Raman signal of primary SERS nanoparticles are described herein. In one embodiment, the process for amplifying a Raman signal associated with primary SERS nanoparticles, wherein the SERS nanoparticles contain a metallic core comprises aggregating secondary SERS nanoparticles about the primary SERS nanoparticles after a binding event between the primary SERS nanotags and a target analyte, wherein the secondary SERS nanoparticles contain a different reporter molecule than the primary SERS nanoparticles or are free from the reporter molecule. In this case, the Raman signal originating from a primary SERS nanoparticle is amplified due to a coupling effect (plasmon effect) between the attached primary SERS nanoparticle and the secondary nanoparticles that are caused to aggregate around the primary SERS nanoparticle.

In another embodiment, the process for amplifying a Raman signal associated with primary SERS nanoparticles comprises binding the primary SERS nanoparticles to a target organism, wherein the primary SERS nanoparticles comprise a reporter molecule for identifying the primary SERS nanoparticles; and binding secondary SERS nanoparticles to the primary SERS nanoparticles, wherein binding the secondary SERS nanoparticles are effective to amplify the Raman signal relative to primary SERS nanoparticles without the bound secondary SERS nanoparticles. In this case, the Raman signal is amplified due to the additive signals arising from the attached primary SERS nanotags, plus the Raman signal from the secondary SERS nanotags that have been enabled to bind to the primary SERS nanotags.

In yet another embodiment, a process for amplifying a Raman signal associated with primary SERS nanoparticles comprises depositing secondary SERS nanoparticles from a solution onto immobilized primary SERS nanoparticles; and aggregating the secondary SERS nanoparticles about the immobilized SERS nanoparticles.

The above described and other features are exemplified by the following figures and detailed description.

DETAILED DESCRIPTION OF EXEMPLARY EMBODIMENTS

The present disclosure is generally directed to amplifying the Raman signal of SERS nanoparticles. In one embodiment, one or more secondary nanoparticles ("amplifier" particles) are brought into close proximity (a few nanometers or less) to the primary SERS nanoparticle, thereby essentially forming a pseudo-like aggregate of nanoparticles clustered around the SERS nanoparticle. The SERS nanoparticles that have the Raman signal amplified by secondary nanoparticles are also referred to herein as the primary SERS nanoparticles.

As noted in the background section, under normal circumstances aggregation is not desirable since it prevents the SERS nanoparticles from being isolated and purified as well as provides limits to their solubility and mobility. In this case, the aggregate is formed after the reporter molecule of the SERS nanoparticle has been formed or after the SERS nanoparticles have been used in an assay. The close proximity of the secondary nanoparticles to the primary SERS nanoparticles provides for further amplification of its Raman signal. These secondary "amplifier" nanoparticles can be forced to aggregate around the primary SERS nanoparticle by specific interactions such as by chemical or biological binding mechanisms, by electrostatic attraction or by non-specific deposition methods such as by evaporative drying of a nanoparticle solution containing the SERS nanoparticle and secondary amplifier nanoparticles. The one or more secondary nanoparticles are similar in geometry and composition to the SERS nanoparticle with the exception that the secondary nanoparticles do not contain the same reporter molecule. In other embodiments the secondary nanoparticles contain a reporter molecule that is different from the one absorbed onto the primary SERS nanoparticles. As such, the secondary nanoparticles do not have to be Raman active but can be merely a stable metal colloid.

Specific interactions between the secondary nanoparticles and the primary SERS nanoparticles can form a sub-monolayer, a monolayer or a multilayer coating on the SERS nanoparticle. Coatings such as glass or a polymer can also be used to cover the SERS nanoparticles, thereby preventing secondary amplifier molecules from directly contacting SERS nanoparticles and allowing for separation of the amplifier molecules from the SERS nanoparticles by a distance dictated by coating thickness (glass or polymer) while still allowing for sufficient amplification. Initial results with glass coated SERS nanoparticles (a glass coating of 5 to 50 nanometers) suggest that the metallic cores need not be touching, but can be separated by the distance dictated by the coating with the amplification effect still being observed. In one embodiment, the distance defined by the coating is less than 5 nanometers.

In another embodiment, assays employing the primary SERS nanoparticle include the use of secondary SERS nanoparticles (i.e., tags), which are targeted to moieties on the primary SERS nanoparticle. In this embodiment, the secondary nanoparticles are SERS active. This process results in increasing the number of SERS active particles bound to the target, either directly, or via their association with the primary particle attached to the target, thereby increasing signal and assay sensitivity. Specifically, the use of the secondary SERS nanoparticles may increase the number of tags associated with each targeted organism for assay and therefore the sensitivity of the assays. Advantageously, the secondary SERS nanoparticles can also include tags with other features as may be desirable for different applications, e.g., superparamagnetism.

By way of example, a sample material that may contain a target organism or molecule is contacted with the primary SERS nanoparticles that have been functionalized with, for example, antibodies, against the target organism. If the target organism is present, the primary SERS nanoparticles will bind to the target organism due to target specific antibodies present of the target organism surface. Unbound primary SERS nanoparticles are then removed in a washing step. Quantities of secondary SERS nanoparticles functionalized with antibodies that bind to the primary SERS nanoparticles are then added. The secondary SERS nanoparticles are Raman active but can also include tags with other features such as superparamagnetism. The unbound secondary SERS nanoparticles are then removed by washing. The above noted process results in an increased number of SERS active particles bound to the target, thereby increasing the signal and assay sensitivity. The sample containing the target molecules or organisms can then be analyzed for Raman intensity using a laser and Raman spectrometer in a manner well known in the art.

The secondary SERS nanoparticles can be exclusively or predominantly SERS active and these can have the same or different Raman signature as the primary SERS nanoparticles. The use of two different Raman signatures can enhance assay specificity by reducing the number of false positives. Moreover, as previously noted, the secondary SERS nanoparticles can include superparamagnetic particles that can be used to immobilize the target complex to reduce background signal.

As a result of the amplification provided by the secondary nanoparticles in either of the processes disclosed above, increased signal intensity, lower limits of detection, and a reduced false positive rate during detection can be obtained. The methods disclosed herein can be used for individually tagging a molecule, cell, bead or solid support to isolate the signal or may be used for multiplexing. Moreover, the amplification process is not intended to be limited to any particular method for producing the SERS nanoparticles, which may or may not include a glass coating.

In accordance with some embodiments, the metallic cores of the nanoparticles are preferably formed from a metal selected from the group consisting of Au, Ag, Cu, Na, Al, Cr as well as alloys. The metal nanoparticles are generally less than 200 nanometers (nm) in diameter. The theory associated with amplification of the Raman signal from SERS nanoparticles (SERS=surface-enhanced Raman scattering) using aggregation-inducing techniques begins with the understanding that existing SERS nanoparticles consist of a nanoparticles having a metallic core to which is adsorbed a reporter molecule, wherein the reporter molecule gives a strong Raman signal due to the surface-enhanced Raman effect. It is believed that the signal from the reporter molecules on the SERS nanoparticles is further amplified when it is sandwiched between the SERS nanoparticles, or between SERS nanoparticles and a planar gold surface. The characteristic signal of the reporter molecule is used to determine the presence and amount of SERS nanoparticles, which can be used in detection schemes (bioassays) of various formats. For example, the SERS nanoparticles can be functionalized with biological molecules as previously noted (e.g., antibodies, DNA, etc) so that they specifically bind to one kind of target organism (e.g., specific types of bacteria, viruses, spores, proteins, DNA, and the like).

The reporter molecule selected for the SERS nanoparticles is not intended to be limited; the selection of which are generally dependent on the particular application. Commonly employed reporter molecules include, but are not limited to, dyes, 1,2-bis(4-pyridyl)ethylene, 4,4'-bipyridyl, 2-qunolinethiol, and 4-mercaptopyridine, and the like. The selection of a reporter molecule for a particular application is well within the skill of those in the art in view of this disclosure.

Figure 2:
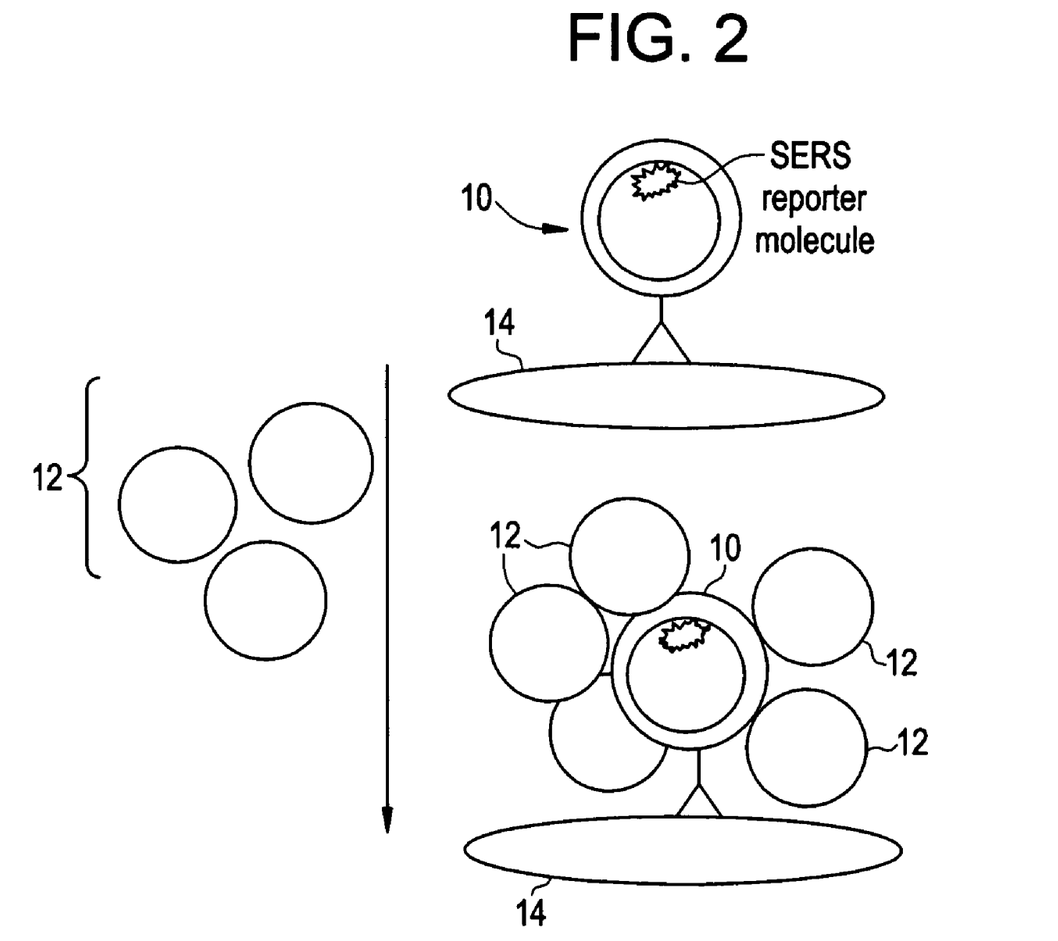
FIG. 2 schematically illustrates aggregation of secondary SERS tags around a primary SERS nanotag after the primary SERS nanotag attached to a target molecule via a bio-recognition event.

As noted above, in one embodiment as shown more clearly in FIG. 2, the one or more of the secondary nanoparticles 12 are brought into close proximity to the primary SERS nanoparticles 10 after bio-recognition of the primary SERS nanoparticles to a target molecule 14, essentially forming a pseudo-like aggregate of nanoparticles clustered around the SERS nanoparticles. Aggregation about the primary SERS nanoparticles can be caused by electrostatic attraction, chemical or biological binding as previously discussed. In this manner, signal amplification can be differentiated from brighter tags. Therefore, one of the advantages provided by embodiments herein includes the use of an aqueous solution and stable reagents to provide the aggregation effect. In one embodiment, SERS-active nanoparticles were modified with an amine in an attempt to create particles with a positive charge to form the secondary SERS nanoparticles. These can be combined with plain or glass-coated SERS-active particles, which have a negative charge such as those produced in accordance with FIG. 1. Aggregation results after the primary SERS nanoparticles have been attached to the target organism resulting in signal amplification upon aggregation of secondary nanoparticles. It should also be apparent that the electrostatic attraction could vary. For example, the primary SERS nanoparticles could have a positive charge and the secondary nanoparticles a negative charge.

Figure 3:
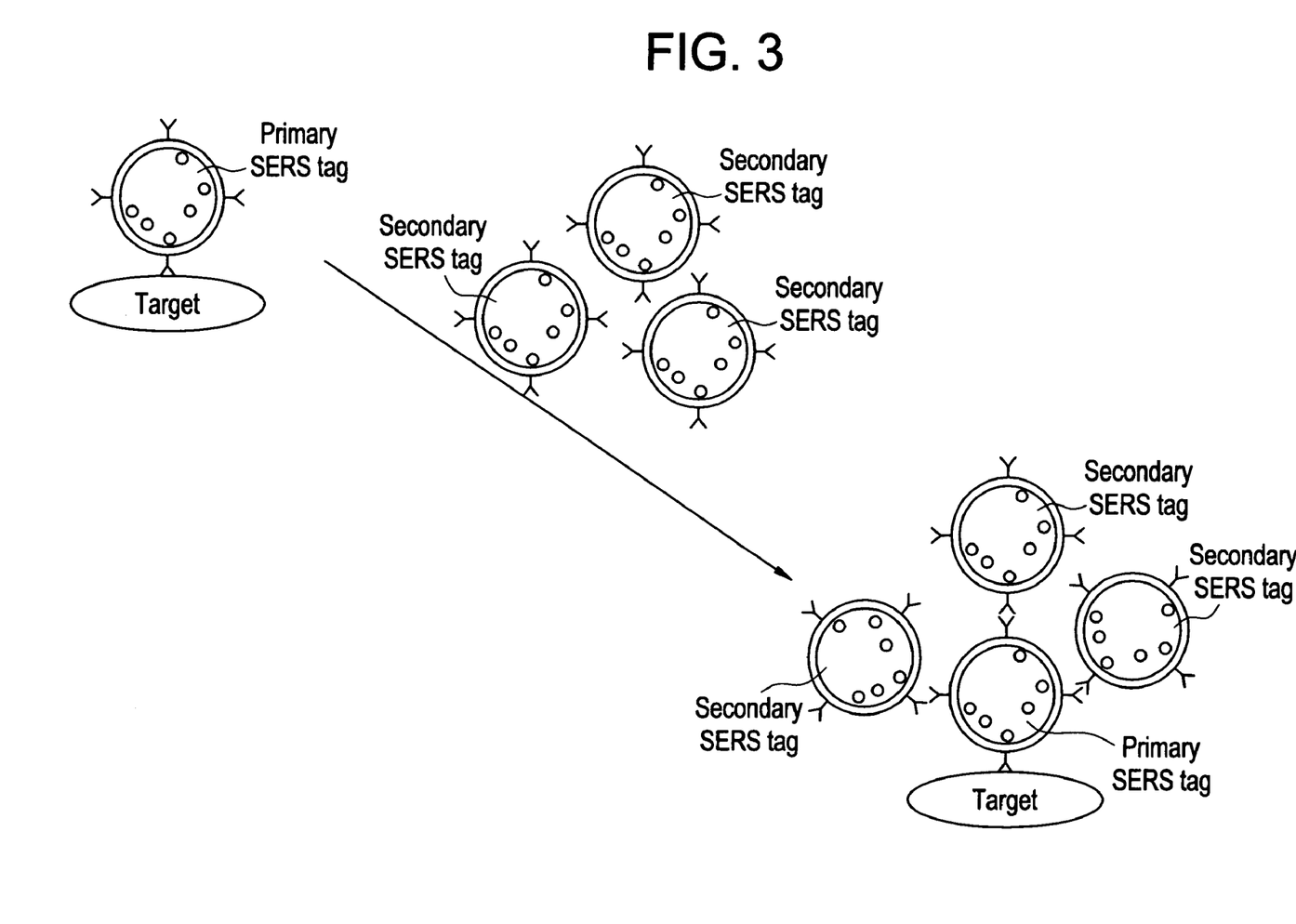
FIG. 3 schematically illustrates binding of secondary SERS particles to a primary SERS particle after the primary SERS particle has been bound to the target analyte.

FIG. 3 schematically illustrates binding of secondary SERS particles to a primary SERS particle after the primary particle bound to a target analyte.

Increasing the Raman signal of individual SERS nanoparticles will improve the detection limit. In a bioassay, the signal from a single binding event (one SERS nanoparticle) can be amplified by the methods disclosed herein in a second step when secondary particles are introduced after the binding event. The Raman signal associated with the single SERS nanoparticles can then be detected because of the amplification. Existing methods for coupling antibodies to surfaces or to other molecules are well known with commercial reagents and protocols readily available to those in the art.

The following examples are presented for illustrative purposes only, and are not intended to limit the scope of the invention.

EXAMPLE 1

In this example, 60 nanometer gold colloid solutions were prepared. A 2 liter, 3-necked round-bottom flask with stirring provided by an electric overhead stirrer (Arrow Engineering #JR4000) with a Teflon® paddle was immersed in an ice bath. Using freshly prepared and pre-cooled reagent solutions, the gold colloid solution was prepared as follows. The glassware was first cleaned with aqua regia (3 parts HCl:1 part $HNO_3$) and between batches of colloid and rinsed with Milli-Q distilled deionized water. A Raman spectrometer consisting of the components from General Electric Company's StreetLab®, and controlled by Ocean Optics software was utilized.

A stock solution of 1% $HAuCl_4 3H_2O$ was prepared by dissolving the solid in Milli-Q distilled deionized water. For example, 2 grams $HAuCl_4 3H_2O$ in about 10 milliliter water, then transfer quantitatively into a 200 milliliter volumetric flask and dilute. The solution was filtered through a 0.2 micron cellulose acetate filter and stored in a dark environment prior to use. A stock solution of 1 Normal NaOH was prepared from a Baker Dilut-it cartridge. Dilute a portion to provide 0.01 Normal NaOH for reagent preparations (500 milliliters diluted to 50 milliliters). The remainder of the ingredients were prepared the day of the synthesis and stored on ice.

A 32% (w/v) trisodium citrate dihydrate solution in 0.01N Normal NaOH was prepared by weighing 3.2 grams (g) trisodium citrate dihydrate in a 10-milliliter tube top which 0.01 Normal NaOH was added to make 10 milliliters. Complete dissolution required several minutes of mechanical agitation.

A 1.6 M hydroxylamine hydrochloride solution was prepared by weighing 1.116 g hydroxylamine hydrochloride in 10 milliliters of Milli-Q water.

Into the assembled flask and stirring assembly, 24 milliliters (ml) of the 1% $HAuCl_4$ stock solution was added to 976 milliliter of (ice cold) Milli-Q water to form 1 liter of 0.024% $HAuCl_4$. To this solution, 1.00 ml of the hydroxylamine solution was added with continued stirring. Exactly 20 minutes after the hydroxylamine was added to the gold solution, 1 ml of a reductant solution was added. The reductant solution was prepared by mixing 1.0 ml of the 32% citrate solution, 525 microliters of 0.01 Normal (N) NaOH, and 75 microliters of the 0.0004% sodium borohydride. Within seconds, the solution changed rapidly in color from yellow to deep purple to red. The solution is stirred for about 1 minute after which the stirring assembly is dismantled and the colloid transferred to a flask at room temperature. An aliquot of the resulting colloid is then diluted with an equal part water before characterization by UV-Visible spectroscopy. The resulting colloids had an absorbance of 1.3-1.5 and $\lambda_{max}$=528-534 nanometers.

EXAMPLE 2

Figure 4:
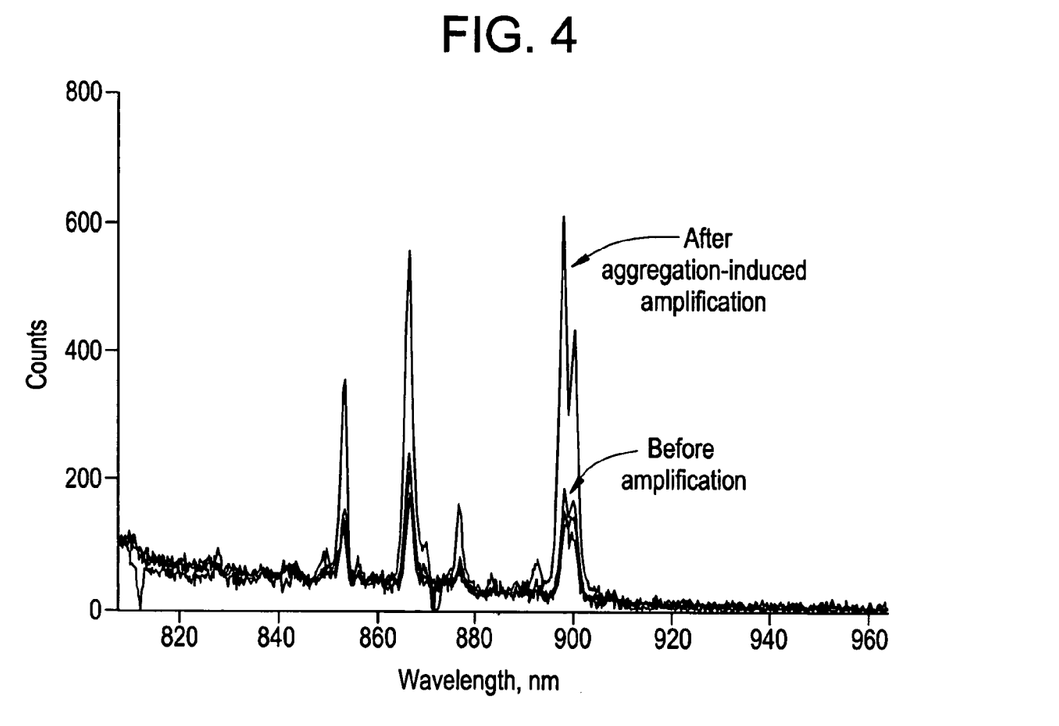
FIG. 4 graphically illustrates overlayed Raman spectra showing the effect of aggregating additional gold colloid onto SERS nanotags [functionalized with a reporter molecule 1,2-bis(4-pyridyl)ethylene (BPE)] that have been immobilized by depositing them onto a filter paper.

In this example, 2 microliters of the gold colloid solution of Example 1 was deposited onto filter paper. To this, a 1 millimole (mM) solution in ethanol of 1,2-bis(4-pyridyl)ethylene (BPE) was deposited. As noted above, BPE is a reporter molecule. To this 6 microliters (μl) of plain colloid was added. The Raman spectrum was periodically measured and is graphically shown in FIG. 4. From the spectra, it was observed that the signal intensity corresponding to the reporter molecule dramatically increased upon addition of the plain colloid, which is indicative of aggregate formation.

EXAMPLE 3

Figure 5:
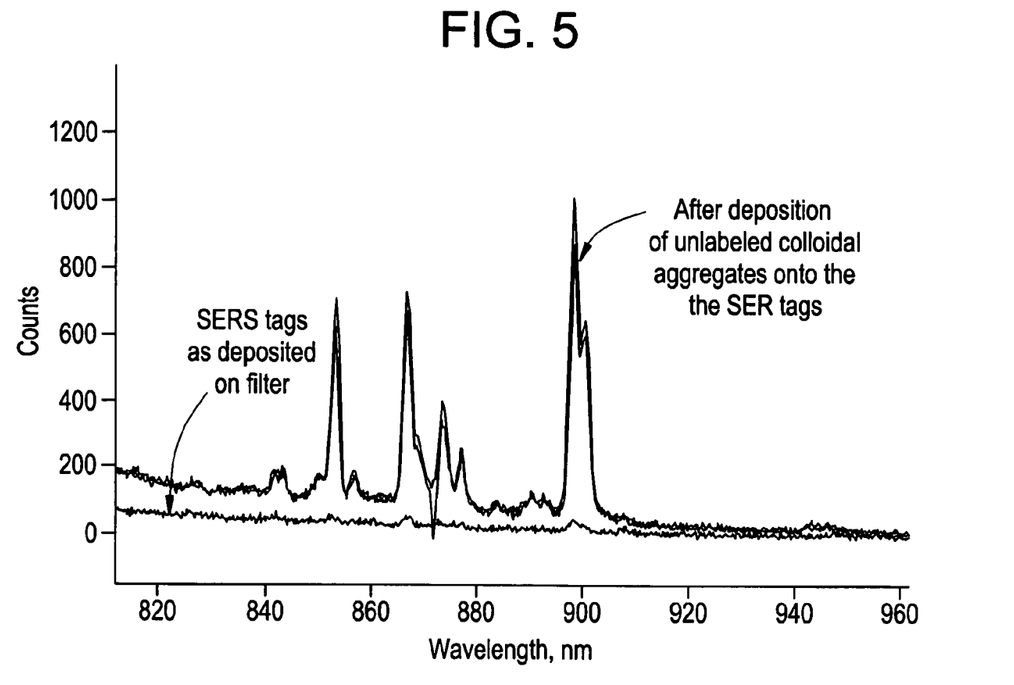
FIG. 5 graphically illustrates overlayed Raman spectra from immobilized BPE-labeled SERS nanotags before and after they were treated with additional unlabeled colloid, under conditions where the unlabeled colloid aggregates around the primary SERS nanotags.

In this example, the colloid and BPE were mixed prior to deposition of 2 μl onto filter media followed by drying. The filter media was a porous hydrophilic acrylic copolymer commercially available under the trade name Versapor from the Pall Corporation. A colloid solution was then added to the colloid/BPE mixture. Raman spectra was periodically obtained, the results of which are provided in FIG. 5. Signal amplification was observed upon addition of the colloid.

The primary SERS nanotags were prepared in situ by first depositing 2 microliters of gold colloid (60 nm diameter, $2.3 \times 10^{10}$ particles/mL) onto the filter paper. One drop of a solution of pre-formed gold nanoparticle aggregates (2 mL colloid plus 1 drop 500 M NaCl) was deposited onto the spot containing the immobilized primary SERS nanotags. The presence of the unlabeled gold nanoparticle aggregates around the immobilized BPE-labeled primary SERS nanotags causes an amplification of its Raman signal.

EXAMPLE 4

Figure 6:
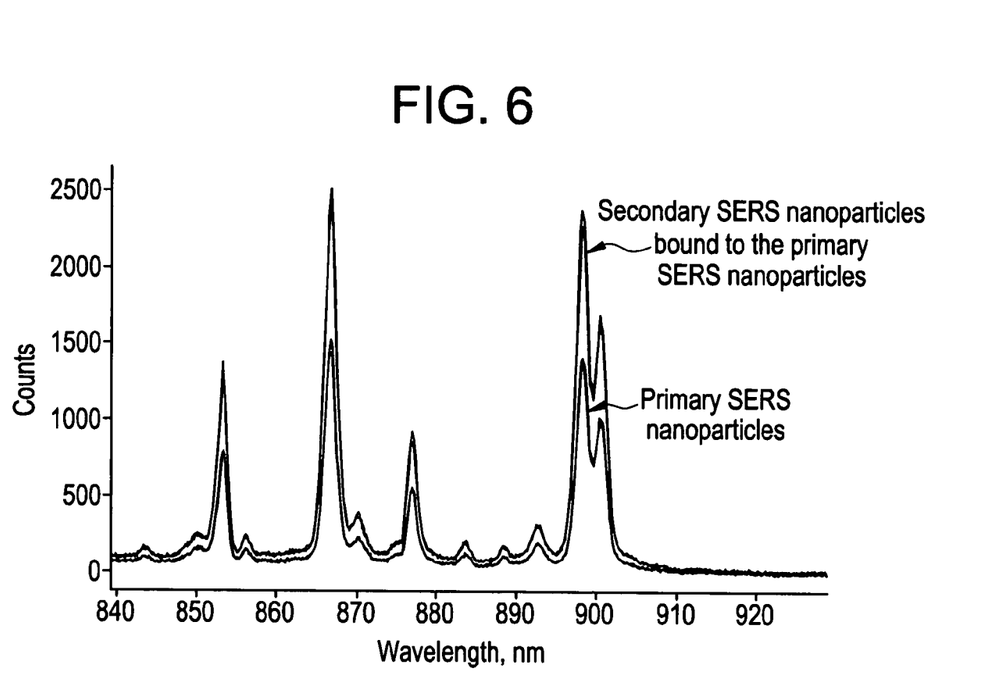
FIG. 6 graphically illustrates overlayed Raman spectra showing the signal of assays performed with primary SERS particles then with primary and secondary SERS particles.

In this example, a solution of primary SERS tags with BPE as the Raman reporter molecule was mixed with a target analyte. The primary SERS tags bound to the target analyte and the excess were washed away. The signal intensity from this assay was observed and the resulting data is shown as the less intense traces in FIG. 6. Secondary SERS tags (also with BPE as the Raman reporter molecule) were then introduced into the system and specifically bound to the primary tags via an antibody interaction and the excess tags were washed away. The signal intensity from this assay was observed and the resulting data is shown in FIG. 6. The traces depicting the lower signal indicate the assay performed with primary tags alone whereas the traces depicting higher signal indicate the assay results when performed with the primary and secondary tags after the binding of the secondary tags. Clearly, it can be seen that signal amplification occurred upon the binding of secondary SERS tags to the primary SERS tags already bound to the target.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. elements with insubstantial differences from the literal languages of the claims.

What is claimed as new and desired to be protected by Letters Patent of the United States is:

1. A process for amplifying a Raman signal associated with primary SERS nanoparticles, wherein the SERS nanoparticles contain a metallic core, the process comprising:
    aggregating secondary SERS nanoparticles about the primary SERS nanoparticles after a binding event between the primary SERS nanoparticle and a targeted analyte, wherein the secondary SERS nanoparticles contain a different reporter molecule than the primary SERS nanoparticles or are free from the reporter molecule.

2. The process of claim 1, wherein the primary SERS nanoparticles have a glass coating of less than 5 nanometers.

3. The process of claim 1, wherein the binding event comprises binding at least one of the primary SERS nanoparticles to a target organism and amplifying the Raman signal associated with the at least one of the primary SERS nanoparticles.

4. The process of claim 1, wherein the metal core contains a metal selected from a group consisting of gold, silver, copper, sodium, aluminum, chromium, and alloys containing at least one of these metals.

5. The process of claim 1, wherein the primary SERS nanoparticles have a negative charge and the secondary SERS nanoparticles have a positive charge.

6. The process of claim 1, wherein the primary SERS nanoparticles have a positive charge and the secondary SERS nanoparticles have a negative charge.

7. The process of claim 1, wherein said aggregating secondary SERS nanoparticles comprises depositing a solution containing the secondary SERS nanoparticles onto the primary SERS nanoparticles; and precipitating the secondary SERS nanoparticles by drying the solution.

8. The process of claim 1, wherein said aggregating secondary SERS nanoparticles comprises destabilizing a solution of the secondary SERS nanoparticles by addition of a destabilizing material and forcing the solution containing the secondary SERS nanoparticles to aggregate about the primary SERS particles.

9. The process of claim 8, wherein said destabilizing a solution of the secondary SERS nanoparticles comprises precipitating a portion of the secondary SERS nanoparticles and forming aggregates about the primary SERS nanoparticles.

10. The process of claim 1, wherein the primary SERS nanoparticles have an average particle diameter of less than 200 nanometers.

11. The process of claim 1, wherein the primary SERS nanoparticles have an average particle diameter at 50 to 100 nanometers.

12. A process for amplifying a Raman signal associated with primary SERS nanoparticles, comprising:
   binding the primary SERS nanoparticles to a target organism, wherein the primary SERS nanoparticles comprise a reporter molecule for identifying the primary SERS nanoparticles; and
   binding secondary SERS nanoparticles to the primary SERS nanoparticles, wherein said binding secondary SERS nanoparticles is effective to amplify the Raman signal relative to primary SERS nanoparticles without bound secondary SERS nanoparticles.

13. The process of claim 12, wherein the secondary SERS nanoparticles contain a different reporter molecule than the reporter molecule of the primary SERS nanoparticles.

14. The process of claim 12, wherein the secondary SERS nanoparticles contain the reporter molecule of the primary SERS nanoparticles.

15. The process of claim 12, wherein the primary and secondary SERS nanoparticles are formed from a metal colloid.

16. The process of claim 15, wherein the metal colloid contains a metal selected from a group consisting of gold, silver, copper, sodium, aluminum, chromium, and alloys containing at least one of these metals.

17. The process of claim 12, wherein the secondary SERS nanoparticles comprise reporter molecules that exhibit superparamagnetism.

18. The process of claim 12, wherein the primary SERS nanoparticles have a negative charge and the secondary SERS nanoparticles have a positive charge.

19. A process for amplifying a Raman signal associated with primary SERS nanoparticles, comprising:
   depositing secondary SERS nanoparticles from a solution onto immobilized primary SERS nanoparticles; and
   aggregating the secondary SERS nanoparticles about the immobilized SERS nanoparticles.

20. The process of claim 19, wherein said depositing secondary SERS nanoparticles comprises precipitating the secondary SERS nanoparticles by drying the solution.

21. The process of claim 19, wherein said depositing secondary SERS nanoparticles comprises destabilizing the secondary SERS nanoparticles solution by addition of a salt or other destabilizing material and forcing the solution containing the secondary SERS nanoparticles to aggregate about immobilized primary SERS particles.

22. The process of claim 21, wherein said destabilizing secondary SERS nanoparticles comprises precipitating a portion of the secondary SERS nanoparticles and forming aggregates about the immobilized primary SERS nanoparticles.

23. The process of claim 19, wherein the primary SERS nanoparticles have a positive charge and the secondary SERS nanoparticles have a negative charge.

* * * * *